United States Patent [19]

Hemmings et al.

[11] Patent Number: 5,321,974
[45] Date of Patent: Jun. 21, 1994

[54] METHOD AND DEVICE FOR DETERMINING RHEOLOGICAL PROPERTIES

[75] Inventors: Raymond T. Hemmings, Mississauga; Edward G. Kimber, Burlington; Hillar Kassfeldt, Burlington, all of Canada

[73] Assignee: Radian Corporation, Austin, Tex.

[21] Appl. No.: 72,502

[22] Filed: Jun. 4, 1993

[51] Int. Cl.[5] .......................................... G01N 11/14
[52] U.S. Cl. ................................................. 73/54.31
[58] Field of Search ................ 73/54.31, 54.32, 54.33, 73/54.35, 54.28, 54.29

[56] References Cited

U.S. PATENT DOCUMENTS

| | | | |
|---|---|---|---|
| 3,875,791 | 4/1975 | Fitzgerald et al. | 73/54.31 |
| 4,062,225 | 12/1977 | Murphy, Jr. et al. | 73/54.35 |
| 4,299,119 | 11/1981 | Fitzgerald et al. | 73/54.32 X |
| 4,524,611 | 6/1985 | Richon et al. | 73/54.35 |
| 4,535,621 | 8/1985 | Gervais et al. | 73/54.23 |
| 4,879,897 | 11/1989 | Booth et al. | 73/54.31 |

OTHER PUBLICATIONS

Tattersall et al., "The Rheology of Fresh Concrete," 1983, pp. 77, 80, 82-83, 87, 89-91, and 262-265.

Primary Examiner—Hezron E. Williams
Assistant Examiner—Joseph W. Roskos
Attorney, Agent, or Firm—Klauber & Jackson

[57] ABSTRACT

A method for the measurement of rheological properties of high density slurry materials and in particular high density mill tailings. A sample of the tailings is placed within a mixing tub, with mixing paddle used to effect the mixing. A digitally controlled electric motor is used to directly drive the paddle at a constant predetermined speed or speeds. Feedback control elements, including a variable speed drive and a computer constantly monitor the mixing speed and compensate for deviations therefrom. The tub is laterally pivotable against a load cell for a direct determination of reaction torque with correlation to viscosity and other rheological properties of the mill tailings. The load cell emits signals which are conditioned and fed to the computer which correlates torque to speed and determines the rheological properties on a continuous real-time basis. The computer also compares determined torque/speed parameters to stored rheological properties of known materials.

11 Claims, 2 Drawing Sheets

METHOD AND DEVICE FOR DETERMINING RHEOLOGICAL PROPERTIES

FIELD OF THE INVENTION

This invention relates to the real time, accurate determination of rheological properties of high density slurry type materials such as concrete and in particular high density mill tailings under rapidly changing conditions.

BACKGROUND OF THE INVENTION

The standard devices in the field of measurement of rheological properties of concrete are described by GH Tattersall and PFG Banfill ("Tattersall"), in chapter 6 of their treatise, *The Rheology of Fresh Concrete* (Pitman Publishing Inc. 1983). The various devices described, all involve the mixing of the concrete in a bowl by either concentric or planetarily movable paddles, driven through an electric motor with an hydraulic transmission. Mixing torque, with correlation to concrete viscosity and other rheological properties of the concrete, is determined by variations in oil pressure in the hydraulic gear box, occasioned by the torque of mixing. Recordation of the variations in oil pressure is used in a subsequent calculation, with reference to the set mixing speed or speeds in order to obtain torque/speed plots, from which the relevant rheological properties are determined.

While such devices provide some measurement of the rheological properties of concrete, there are inherent properties of the system which result in substantial measuring errors. Since the mixing torque is measured by monitoring oil pressure in the hydraulic gearbox there is no allowance for energy losses in the drive system between the hydraulic gearbox and the mixing paddle. In addition, there is no provision for oil temperature corrections which cause pressure and measurement deviations.

Another source of error in the Tattersall system is the measurement of paddle speed which requires the use of calibration curves of torque versus speed at various speed settings of the hydraulic gearbox and interpolation for intermediate speed settings. Unknown deviations of paddle speed may occur, with continued mixing, caused by changes in mixing torque.

In addition, while the Tattersall device provides some degree of accuracy with concrete, its indirect torque measurements are not suitable for accurate measurement of the rheological properties of high density mill tailings, which have completely different "aggregate" gradations, and different water to solids ratios by an order of magnitude. The tailings also interact chemically with the binder system, with deviations resulting from different products and their rheological properties, as well as diminution of reactant materials.

DESCRIPTION OF CO-PENDING APPLICATION

In co-pending U.S. application Ser. No. 08/072,980, filed on even date herewith (the disclosure of which is incorporated herein by reference thereto), a device for measurement of rheological properties is described in which the measurement defects of the Tattersall devices are compensated for. Specifically, the co-pending application describes the use of a device for direct measurement of mixing torque, as opposed to the indirect oil-pressure monitoring of the Tattersall devices. Oil temperature corrections, with pressure and measurement deviations are obviated as factors in the accuracy of mixing torque measurements.

In order to directly measure the mixing torque, the device is provided with means for permitting the container to move during the mixing with a displacement directly related to the torque of the mixing. Monitoring means is included, for monitoring torque-induced displacement of the container for direct determination of the torque of mixing and the rheological properties of the material.

Specifically, the device comprises a digitally controlled electric motor mounted directly to a reducing gearbox, with helical gears, to ensure smooth operation. The motor, gearbox and paddle are mounted in a substantially fixed position, relative to the container, which is mounted in a vertically movable manner, whereby the paddle can be readily immersed and removed from the material being tested.

However, in contrast to the Tattersall device, as well as other devices in the field, the container or tub containing the sample material is displaced during mixing, with low friction losses, in a plane horizontal to the mixing torque, whereby such displacement is in direct relation to the mixing torque.

The low friction loss, horizontal-plane displacement of the tub is effected by mounting the tub on a swivel plate support, which is mounted on a fixed plate. Roller bearing elements support the swivel plate and keep the swivel plate support and fixed plate in stable, spaced, though relatively movable relation. The torque of mixing causes the tub, with swivel plate support, to swivel on the surface of the fixed plate. This motion between the two plates is restrained by a load cell, whereby torque reacting on the swivel plate causes a proportional straining of the load cell.

The load cell emits an electrical signal directly proportional to the torque experienced by the swivel plate. The signal is then recorded on an x-y chart recorder for torque/speed data acquisition and subsequent correlation, to rheological properties of materials such as viscosity characteristics.

Because the reaction torque is monitored directly on the tub, mechanical losses in the drive train to the paddle, which may be quite large, are of no consequence in the reaction torque determination.

However, despite the advantages obtained with the direct torque measurement device of the co-pending application, the inherent complicated nature of the rheology of mill tailings can cause uncompensated for errors. Thus, during mixing, changes can and do occur in viscosity of the material which will tend to cause unknown variations in mixing speed, despite specific mixing speed settings. In addition, because of the rapid rate of change in the rheology, normal recordation such as with the standard x-y chart recorders, effectively miss such changes in accurately determining the rheological properties.

SUMMARY OF THE INVENTION

It is an object of the present invention to provide a method for the accurate and rapid real-time acquisition of data regarding rheological property measurement of both concrete and high density mill tailings from direct measurement devices.

It is a further object of the present invention to provide such method for the rheological property measurement of mill tailings with speed feedback compensation for variations in mixing torque.

These and other objects, features and advantages of the present invention will become more evident from the following discussion and drawings in which:

SHORT DESCRIPTION OF THE DRAWINGS

FIG. 1 depicts a partially sectioned elevational schematic view of the device used in the present invention; and FIG. 2 is a schematic representation of the operation of the method of the present invention.

DETAILED DESCRIPTION OF THE INVENTION

Figure 1:
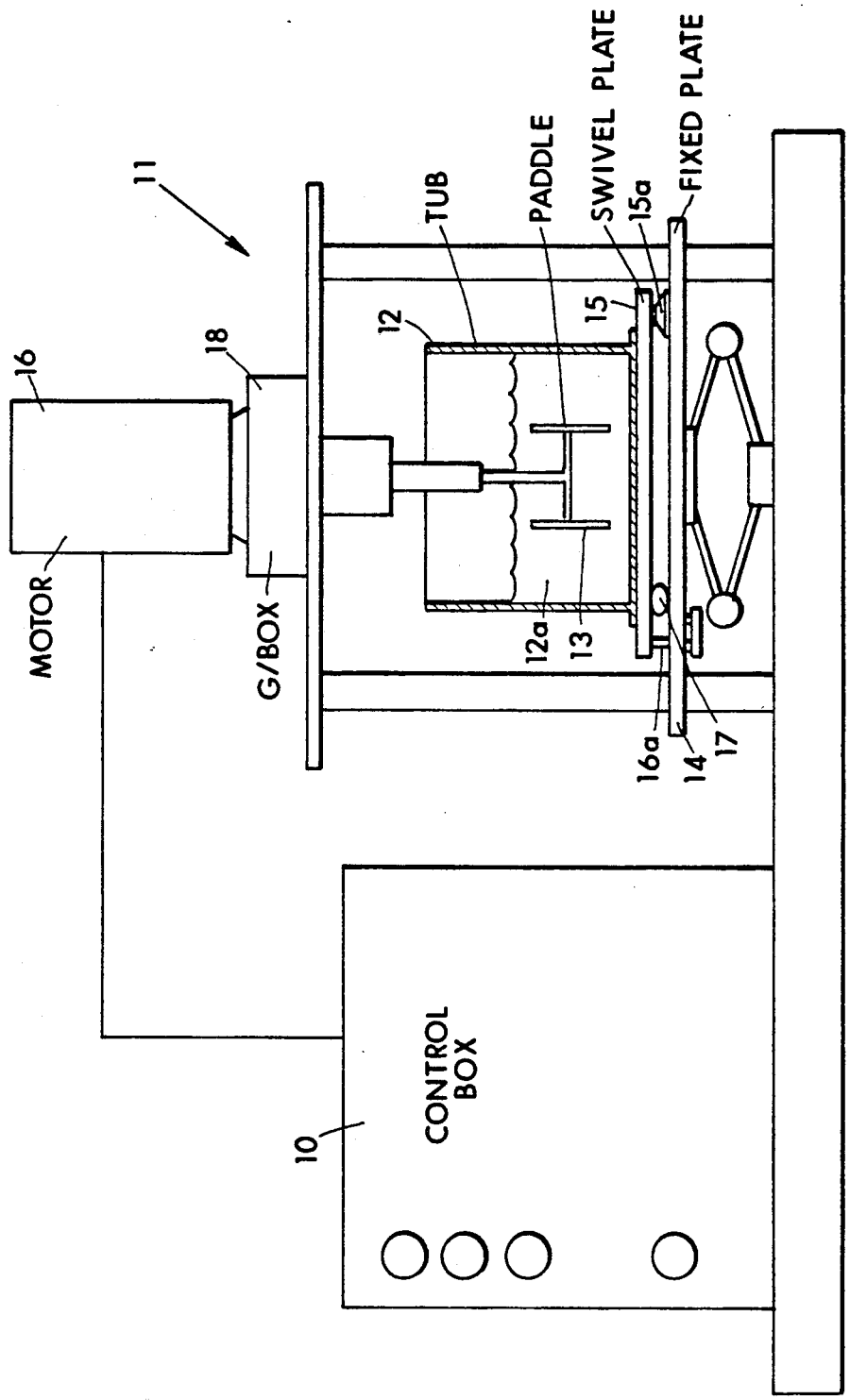

Generally the present invention comprises a method for improving the accuracy and speed of data acquisition of direct rheological measurements of mill tailings, concrete and other Bingham, dilatant and pseudoplastic materials. In accordance with the present invention, the direct measurement rheometer of the co-pending application is linked to feedback control means which instantaneously compensates for changes in mixing impeller speed caused by viscosity changes and the like. In effecting such feedback control, it is preferred that a computer with preprogrammed impeller speed parameters is linked to an electronic variable speed drive which controls the impeller speed. Variations in impeller speed are constantly monitored by the computer with appropriate corrections to maintain the required speed or speeds. Appropriate software can control the time spent at any one speed to less than one revolution of the impeller.

As long as the impeller speed is known at a particular time, its relation to the directly measured torque at that time can be correlated, in an accurate determination of the viscosity and other rheological characteristics of the particular mill tailing or similar material. Thus, a typical measurement run can constitute from 10 to 20 descending and ascending impeller speeds (less speeds are used in a rapidly changing system and more speeds are used in a stable system).

In order to effect the appropriate correlation for speed control and for the appropriate acquisition of data, it is important that the torque data be continuously acquired and correlated during the test runs. In accordance with the present invention, during a "test run", continuous torque or reaction data from the rheometer load cell are fed to a computer through a signal conditioner, generally in the form of a pre-amplifier. Since the output of the load cell is in analog form, means, such as a pc interface card, are utilized for analog/digital conversion and input into the computer processing unit.

The input of the complex waveforms produced by the load cell of the rheometer is converted, by appropriate correlative software, in conjunction with the known impeller speed, to provide conventional torque/speed output plots, from which are calculated the values of plastic viscosity and yield stress of the tested material. The shape of the resulting torque/speed plots provide an indication of the flow type (e.g. Bingham, dilatant, pseudoplastic, etc.), together with any hysteresis or time-dependent phenomena which may be occurring during the test run.

With the instantaneous monitoring of both impeller speed and torque values, and feedback control, it is possible to accurately measure rheological data. Such accuracy is possible, despite the presence of a system undergoing rapid change such as by internal chemical processes, including cementation in a concrete or through relaxation phenomena, such as those present in high density paste systems.

DETAILED DESCRIPTION OF THE DRAWINGS AND THE PREFERRED EMBODIMENT

With specific reference to the drawings, in FIG. 1, the rheological measurement device 11, as described in the co-pending application, comprises a digitally controlled electric motor 16 directly in line with gear box 18 without intervening hydraulic transmission. H-configured paddle 13 is thus directly driven by motor 16 without an intervening hydraulic transmission. In accordance with the present invention, monitoring of the speed of the motor shaft of paddle 13 provides the feedback between paddle 13 (stiffly mechanically coupled thereby with the motor with assumed accurate control of paddle speed) and motor 16 during mixing of mill tailings 12a. This enables the device 11 to maintain a constant speed or constantly monitored known speeds. Swivel plate 15, which directly supports mixing tub 12 containing the mill tailing 12a, is connected to fixed support plate 14 via pivot 15a containing a horizontally disposed roller bearing member (not shown). Control box 10 permits mixing speed control with feedback and provides an informational conduit to a computer control for analysis of measured mixing torque.

Figure 2:
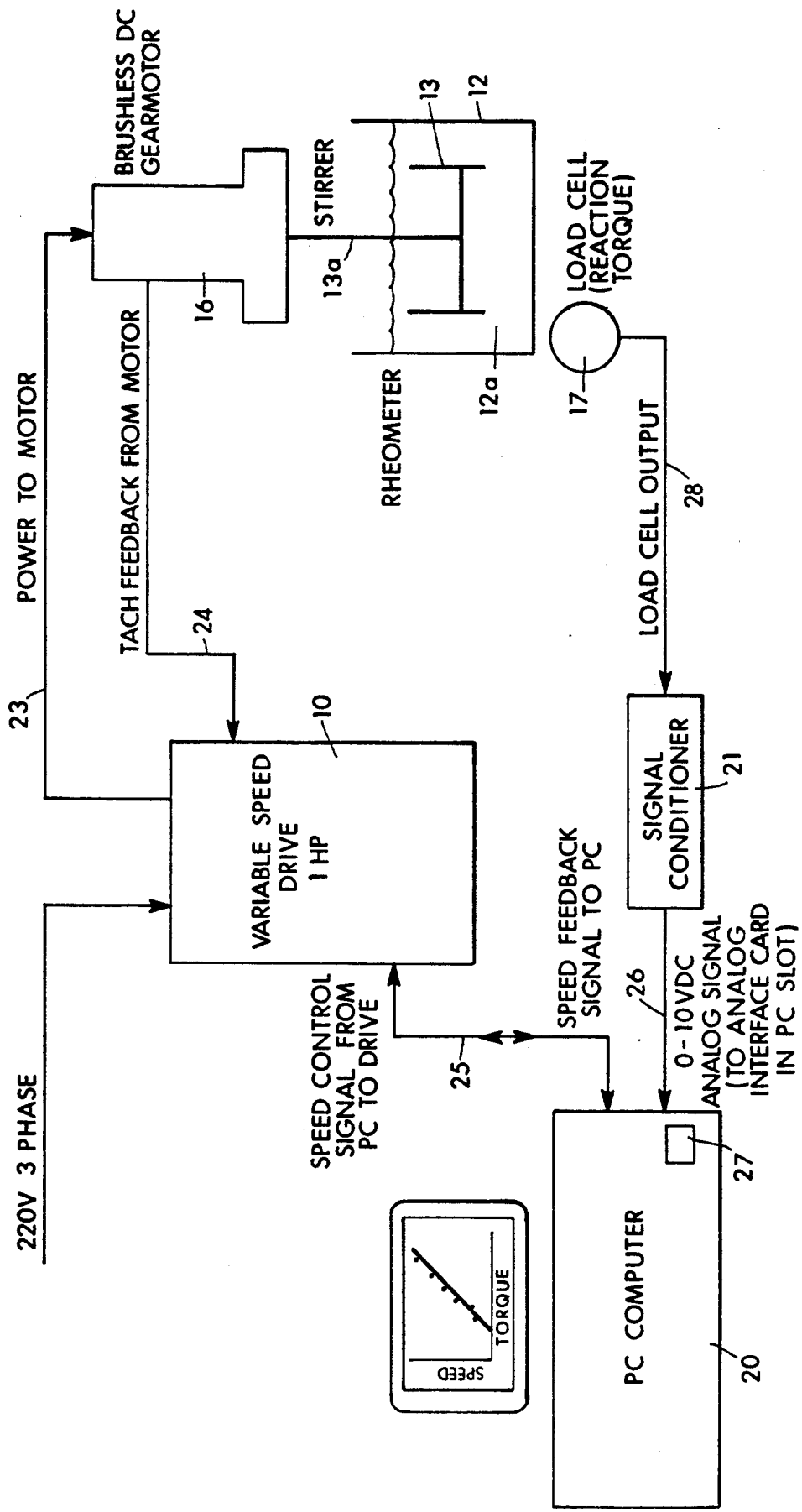

As is more clearly seen in FIG. 2, the motor 16 is a brushless DC gear motor directly linked to the mixing paddle 13 by paddle shaft 13a. Direct feedback between motor 16 and mixing paddle 13 via rotation of paddle shaft 13a is an accurate real-time measurement of the actual paddle speed, as affected by rapid changes within the sample 12a during mixing.

Variable speed drive 10 (control box) provides power 23 to the motor 16 and receives a tach feedback 24 from the motor 16. The motor speed feedback 25 is then fed to pc computer 20 and signals for speed correction are returned to the variable speed drive 10, on an almost instantaneous basis.

At the same time, signals 28 from load cell 17, indicating reaction torque of the tested sample 12a, are transmitted through signal conditioner 21 and analog/digital converter 27 for monitoring by pc computer 20. The reaction torque signals are then correlated, on a real-time ongoing basis, with the mixing speed signals, for the continuous plotting of a speed/torque plot for the determination of the rheological properties of the sample material 12a. With appropriate software the computer 20 calculates and displays or otherwise directly reports the rheological properties of viscosity, shear stress and the like. Rheological tables contained within computer memory are also referred to, in order to match the properties of the tested materials with those of other materials having known properties. An ongoing material profile can accordingly be generated as a double check for property evaluation.

It is understood that the above description and drawings are illustrative of the present invention and that changes in testing device structure, computer control with feedback and monitoring operations, are possible without departing from the scope of the present invention as defined in the following claims.

What is claimed is:

1. A method for the rheological property determination of a slurry type material, comprising the steps of:

a) placing a sample of said slurry type material into a container;
b) mixing the sample, within the container, at one or more substantially known rates of speed, wherein the container moves, during the mixing, with a displacement directly related to the torque of the mixing;
c) monitoring the displacement of the container, during said mixing, for direct determination of the torque of mixing and the rheological properties of the slurry sample;

the improvement comprising the steps of constantly monitoring the speed, at which the sample is being mixed, with feedback control means, and wherein said feedback control means continuously, and substantially instantaneously, compensates for deviations, from the one or more substantially known rates of speed, caused by said mixing, in order to constantly maintain the one or more substantially known rates of speed.

2. The method of claim 1 wherein said feedback control means comprises an electronic variable speed drive operatively linked to a computer having preprogrammed instructions for the compensation of deviations from the one or more substantially known rates of speed.

3. The method of claim 2, wherein said material comprises mill tailings.

4. The method of claim 2, wherein the means for mixing the sample comprises a digitally controlled electric motor, a mixing paddle, and a direct drive between the motor and paddle.

5. The method of claim 4, wherein the feedback control means ensures that the paddle substantially maintains the one or more known rates of speed throughout the mixing, regardless of the torque required to mix the sample, even with variations in rheology and/or temperature.

6. The method of claim 5, wherein the paddle speed is infinitely variable over a range of speed required to effect the mixing.

7. The method of claim 2, wherein the monitoring means comprises a load cell, wherein displacement of the container during mixing causes deflection of the load cell, said deflection being monitored as an output signal.

8. The method of claim 7, wherein the output signal is conditioned and continuously transmitted to the computer for correlation with correlative values, stored within said computer, to rheological properties of materials which provide a measured torque at the one or more known rates of speed of mixing.

9. The method of claim 8, wherein the output signal is in the form of complex waveforms, and wherein said computer contains correlative software, whereby the one or more substantially known rates of speed are correlated to the output signal to provide torque/speed output plots, with values of plastic viscosity and yield stress of the sample being continuously determined by said computer.

10. The method of claim 9, wherein the values of viscosity and shear stress are determined when the sample is undergoing rapid change by internal chemical or physical processes during said mixing.

11. The method of claim 9, wherein the computer contains rheological tables, whereby the computer continuously compares torque/speed output plots to said tables, in order to match the properties of the sample with those of other materials having known properties.

* * * * *